United States Patent [19]

Mack et al.

[11] Patent Number: 5,476,948
[45] Date of Patent: Dec. 19, 1995

[54] PREPARATION OF 5-ACETOACETYLAMINO-2-BENZIMIDAZOLONE

[75] Inventors: Karl E. Mack, Wiesbaden; Michael Bohusch, Neu Anspach, both of Germany

[73] Assignee: Hoechst Aktiengesellschaft, Frankfurt am Main, Germany

[21] Appl. No.: 325,780

[22] Filed: Oct. 19, 1994

[30] Foreign Application Priority Data

Oct. 19, 1993 [DE]  Germany ............................ 43 35 614.1

[51] Int. Cl.⁶ .................................................. C07D 235/24
[52] U.S. Cl. ............................................................ 548/306.4
[58] Field of Search ........................................... 548/306.4

[56] References Cited

U.S. PATENT DOCUMENTS

| | | | |
|---|---|---|---|
| 4,087,610 | 5/1978 | Sahm et al. | 548/306.4 |
| 4,153,798 | 5/1979 | Heise et al. | 548/306.4 |

FOREIGN PATENT DOCUMENTS

| | | |
|---|---|---|
| 1795051 | 4/1972 | Germany . |
| 2518922 | 11/1976 | Germany . |
| 2612391 | 10/1977 | Germany . |
| 57-126453 | 8/1982 | Japan . |
| 5213896 | 8/1993 | Japan . |

*Primary Examiner*—Joseph K. McKane
*Attorney, Agent, or Firm*—Connolly and Hutz

[57] ABSTRACT

A process for preparing 5-acetoacetylamino-2-benzimidazolone by continuous reaction of 5-amino-2-benzimidazolone with diketene comprises carrying out the reaction in the presence of a water-soluble $(C_1-C_4)$-alcohol or of a mixture of this alcohol with water at the boiling temperature.

6 Claims, No Drawings

PREPARATION OF 5-ACETOACETYLAMINO-2-BENZIMIDAZOLONE

5-Acetoacetylamino-2-benzimidazolone is an important starting material for the synthesis of water-insoluble monoazo dyes. DE-A-1795051, which concerns the synthesis of these dyes, mentions that 5-acetoacetylamino-2-benzimidazolone can be obtained by reacting 5-amino-2-benzimidazolone with diketene in water or organic solvents, e.g. acetic acid, but details, for example of reaction conditions, are not given.

GB-770263 discloses reacting water-insoluble primary aromatic amines with diketene in the form of their water-dissolved salts of various acids without the temperature being allowed to exceed 50° C. If, however, 5-amino-2-benzimidazolone is reacted by the process described therein, the acetoacetyl compound is obtained only in inadequate purity.

DE-C-2518922 proposes reacting 5-amino-2-benzimidazolone, which is virtually insoluble in water at room temperature, after conversion into salts of various acids at from 60° to 100° C. with diketene in aqueous solution. Owing to the increased solubility of the salts and the proposed rapid addition ("in one shot"), it is true that high space-time yields are obtained in batchwise reactions, but the yield of 5-acetoacetylamino-2-benzimidazolone is lower than 85%.

The reaction of dissolved primary aromatic amines with diketene is also described in JP-A2-57-126453. Here the amines are preferably dissolved in alcohol and reacted at not more than 50° C. by gradual addition of diketene. A possible advantageous application of this procedure to the preparation of 5-acetoacetylamino-2-benzimidazolone is complicated by the fact that, at the stated temperatures, only very dilute solutions of the amine at about 2% by weight in, for example, methanol or ethanol can be used. Moreover, the long reaction times of at least one hour mitigate against the industrially interesting utilization of the process in continuous form.

DE-A-1518881 discloses carrying out the reaction of aromatic amines with diketene in water continuously at temperatures of not more than 50° C. The fact that the reactants are metered in slowly again points to long reaction times and large apparatus dimensions. Owing to the poor solubility of the amines in water, contamination of the products through coprecipitated amine must additionally be taken into account. If this process were applied to the virtually water-insoluble 5-amino-2-benzimidazolone, these problems would worsen.

DE-C-2612391 therefore proposes reacting 5-amino-2-benzimidazolone, or else its salts of selected acids, continuously in aqueous solution with diketene at temperatures of up to 90° C. However, the solubility of 5-amino-2-benzimidazolone in water limits even at 90° C. the concentration of the starting solution to about 4% by weight and on reaction of the amine solutions concentrated at a maximum temperature of 90° C. with diketene at lower reaction temperatures of only 80°–85° C. or even 60° C. (maximum amine concentration of a solution about 1.5% by weight) makes it likely for the amine to precipitate and appear as impurity in the product. DE-C-2612391 further proposes cooling the exothermic reaction for example by the continuous addition of cold water, incurring, however, a further dilution of the reaction mixture. This contributes to the loss of product into the waste water of the process and limits the yield based on amine to about 90%.

In the light of these restrictions and disadvantages there is a great need for an improved process whereby the disadvantages of existing processes are avoided and good to very good yields, high purity and shortened reaction times are made possible, which is simple to carry out in apparatus terms, and which leads only to minimal waste water pollution.

This object is achieved by a process for preparing 5-acetoacetylamino-2-benzimidazolone by continuous reaction of 5-amino-2-benzimidazolone with diketene, which comprises carrying out the reaction in the presence of a water-soluble ($C_1$–$C_4$)-alcohol or of a mixture of this alcohol with water at the boiling temperature.

The reaction is generally carried out by metering diketene and a hot-saturated solution of 5-amino-2-benzimidazolone, separately but simultaneously and continuously into a reactor as reactants. Owing to the heat of reaction released spontaneously, the reactor contents start to boil. The vapors are condensed and the condensate is recirculated, for example into the reactor. The 5-acetoacetylamino-2-benzimidazolone which forms partly crystallizes out during the reaction and is withdrawn from the reactor in the form of a suspension at the rate at which the starting components are added. The isolation of the product can subsequently be carried out batchwise or advantageously continuously. The starting solution of the amine may contain, as the alcohol, methanol, ethanol, one of the propanols or butanols, or else a mixture of one of these alcohols and water. In the last-mentioned case, it is advantageous to use an alcohol which is miscible with water at room temperature in any proportion, such as methanol, ethanol, n-propanol or isopropanol.

The boiling points of the advantageous alcohols are about 65° C. in the case of methanol and about 98° C. in the case of n-propanol. Approximately the same boiling range from about 65° C. to 100° C. is covered by the mixtures of the alcohols with water, so that any desired boiling temperature, i.e. reaction temperature, can be set by means of a suitable composition. The nature of the alcohol and its proportion in the aqueous mixture also determines the maximum solubility of 5-amino-2-benzimidazolone. For instance it is possible to prepare solutions containing about 12% by weight of amine from methanol with 20% by weight of water or else from ethanol with 50% by weight of water, and these solutions have different boiling points of, respectively about 70° C. and about 83° C. By contrast, pure water gives at these temperatures only amine concentrations of, respectively, about 1.5% by weight and about 3% by weight.

The nature of the alcohol used, the presence of water, the boiling points, i.e. the reaction temperatures—possibly influenced by altered pressure—and the dissolving power for the amine are subject to a complex relationship. The huge scope for variation in the parameters thus makes it possible to optimize the reaction conditions from many and varied aspects, for example existing machinery, special quality requirements of the product or even the use of dried or water-moist amine.

It has proved advantageous to limit the reaction temperatures to about 95° C. for safety reasons on account of the thermal instability of the diketene and, in order that sufficiently rapid reactions shall be made possible, to use temperatures above 65° C. It will in many cases be advantageous to use temperatures from 70° C. to 90° C. The temperature of the feed stream of the dissolved amine should always be only slightly below the reaction temperature in order that maximum amine concentrations may be ensured. The diketene stream is generally not preheated. It is further advantageous to carry out the reaction in general under atmospheric pressure. Super-atmospheric or reduced pressure influence the reaction temperature and are therefore only of limited use within the stated temperature range to be used.

An advantageous embodiment of the novel process is, for example in the case of amine which is industrially available in water-moist form, the use of ethanol with 45 to 55% by weight of water for dissolving the amine and the continuous reaction with diketene at 83° C. to 85° C. under reflux.

The step of isolating the 5-acetoacetylamino-2-benzimidazolone from the workup stream will leave some of the product in the mother liquor, according to its solubility. The highly selective reaction of the novel process makes it possible to recirculate the mother liquor for reaction by using it to dissolve the amine, without any significant deterioration in the quality of the product. In this way, after the reaction has taken place, the product in the mother liquor can be substantially recovered with a distinct increase in the yield. The recirculation of the mother liquor therefore constitutes a preferred embodiment of the novel process.

Suitable reactors for the reaction are apparati in which, on the one hand, intensive mixing of the starting components is possible, for example by means of stirrers, by means of static mixers or by means of nozzle systems. On the other hand, evaporative cooling shall ensure optimum heat removal and constancy or limitation of the reaction temperature for a technically safe reaction management. Suitable reactors include for example stirred kettles or stirred kettle cascades, optionally with metering of the starting components via static mixers or mixing nozzles to enhance the mixing effect. Further suitable reactors include typical evaporation apparati, for example circulatory evaporators or falling-film or thin-film evaporators, each equipped with a mixing unit for the feed streams. Owing to the rapid reaction of amine and diketene, high throughput rates can be achieved in the reactor of about 50 kg to 150 kg of feed solution per hour per liter of reactor volume. Owing to the high amine concentration of above 10% by weight, from about 10 kg to 25 kg of product can be produced in the reactor per hour and per liter of reactor volume.

Catalysts are generally not required in the reaction, but can be used in known manner to further speed up the reaction. Suitable catalysts include protic acids, for example acetic acid, amines such as triethylamine or else ammonium compounds. Other additions such as color-lightening substances are generally not necessary, although it is advantageous in particular cases, for example particularly in the case of the use of a particularly dark-colored amine, to add small amounts, for example of dithionite, in the course of the reaction.

The workup of the suspension continuously removed from the reactor is effected in known manner by cooling to complete the crystallization of 5-acetoacetylamino-2-benzimidazolone and isolation on a suitable filter. The mother liquor obtained can generally be re-used as solvent for the starting amine.

The crude product obtained is generally washed, for example with a small amount of alcohol or aqueous alcohol, to remove adherent mother liquor, and the purified product is if necessary dried or freed of alcohol by gentle distillation in an aqueous suspension, and isolated as a water-moist product. Following distillative recovery of aqueous alcohol from the small amount of wash liquor obtained, the novel process produces virtually no waste water.

The novel process is notable for high work safety owing to the boiling of the reaction mixture and the attendant technically simple and effective evaporative cooling and owing to the temperature limitation. Furthermore, large amounts of product are obtained in small reactor volumes owing to the short reaction times and high concentrations of above 10% by weight for the amine feed solution. It is also a feature of the novel process that the mother liquor obtained on product isolation, which still contains product, is re-used as solvent for the amine in further reaction cycles. In this way it is possible to run the process, especially in the case of the use of aqueous alcohols, virtually without the production of waste water and by further product isolation to increase the yield to about 96% based on amine.

The Example illustrates the process.

EXAMPLE

An 82° C. solution of 2.86 kg (19.2 mol) of 5-amino-2-benzimidazolone and 24 kg of ethanol containing 50% by weight of water is metered per hour continuously and simultaneously with 2.06 kg (24 mol) of diketene (purity 98%) into a reactor equipped with a stirrer, reflux condenser, thermometer and, at the bottom, with a run-off. The light-colored suspension in the reactor is refluxed at about 85° C. with stirring and is kept to a constant volume of about 0.3 l by pumping out. The removed suspension is cooled down to about 15° C., and the light-colored crystals are separated by filtration from 22 kg per hour of mother liquor, washed with on average 6 kg per hour of 50% strength ethanol and dried, leaving 4.03 kg (17.3 mol) per hour of 5-acetoacetylamino-2-benzimidazolone as a virtually white crystalline powder. The yield based on amine is 90%.

The mother liquor obtained is re-used in four further reaction cycles by using it at 80° C. to replace fresh ethanol containing 50% by weight of water for dissolving 2.86 kg per hour of 5-amino-2-benzimidazolone at such a rate that 26.86 kg per hour of amine solution can be reacted as described above with 2.06 kg per hour of diketene. Workup gives 4.25 to 4.34 kg per hour of 5-acetoacetylamino-2-benzimidazolone of consistent quality, corresponding to a yield of 95 to 97% based on amine.

What is claimed is:

1. A process for preparing 5-acetoacetylamino-2-benzimidazolone by continuous reaction of 5-amino-2-benzimidazolone with diketene, which comprises carrying out the reaction in the presence of a water-soluble $(C_1-C_4)$-alcohol or of a mixture of this alcohol with water at the boiling temperature.

2. The process of claim 1, wherein the alcohol used is methanol, ethanol, n-propanol or isopropanol.

3. The process of claim 1, wherein the alcohol or alcohol-water mixtures has a boiling point from 65° C. to 100° C.

4. The process of claim 1, wherein ethanol containing from 45 to 55% by weight of water is used.

5. The process of claim 1, wherein the alcohol or alcohol-water mixture is used in the form of recirculated mother liquor.

6. The process as claimed in claim 3, wherein the alcohol or alcohol-water mixture has a boiling point of from 70° C. to 90° C.

\* \* \* \* \*